United States Patent [19]

Winter et al.

[11] 4,070,373
[45] Jan. 24, 1978

[54] TRICYCLIC AMINOALKYL DERIVATIVES

[75] Inventors: Werner Winter, Heppenheim; Max Thiel, Mannheim, both of Germany; Kurt Stach, deceased, late of Mannheim, Germany; by Werner Plattner, administrator, Linz, Austria; Wolfgang Schaumann, Heidelberg; Karl Dietmann, Mannheim, both of Germany

[73] Assignee: C.F. Boehringer & Soehne GmbH, Mannheim-Waldhof, Germany

[21] Appl. No.: 291,426

[22] Filed: Sept. 22, 1972

Related U.S. Application Data

[63] Continuation of Ser. No. 646,170, June 15, 1967, abandoned.

[30] Foreign Application Priority Data

July 21, 1966 Germany .............................. 1568145

[51] Int. Cl.[2] .......................................... C07D 313/12
[52] U.S. Cl. .................................. 260/333; 542/415; 260/327 B; 260/328; 260/335; 260/570.7; 424/275; 424/278; 424/283; 424/330
[58] Field of Search ........................................ 260/333

[56] References Cited

FOREIGN PATENT DOCUMENTS 1,128,938 10/1968 United Kingdom.
1,129,029 10/1968 United Kingdom.

*Primary Examiner*—Norma S. Milestone
*Attorney, Agent, or Firm*—Burgess, Dinklage & Sprung

[57] ABSTRACT

Novel tricyclic aminoalkyl derivatives are disclosed which are characterized by valuable pharmacological activities and namely by cardiac and circulatory activities. The tricyclic aminoalkyl derivatives are compounds of the formula:

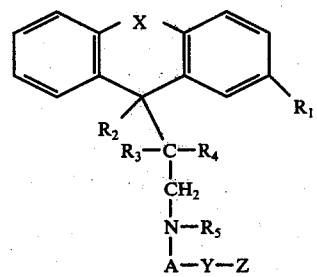

wherein X is an oxygen or a sulfur atom, a saturated or unsaturated, straight chain or branched alkylene group containing up to 3 carbon atoms, an oxymethylene, thiamethylene or thiaethylene group or a valency bond, $R_1$ is hydrogen, halogen, alkyl, alkoxy or trifluoromethyl, $R_2$ is hydrogen or hydroxyl, $R_3$ is hydrogen or together with $R_2$ represents a further valency bond, $R_4$ and $R_5$ which may be the same or different are each hydrogen or lower alkyl, A is alkylene which is substituted by an optionally acylated hydroxyl group, Y is an oxygen or sulfur atom or an optionally alkylated imino group and Z is aryl, aralkyl, cycloalkyl or cycloalkylalkyl which may be substituted by halogen, hydroxyl, nitro, amino, alkoxy, aralkoxy, alkyl, trifluoromethyl, alkylamino or alkylsulfonyl group, and the acid addition salts thereof with pharmacologically acceptable acids.

19 Claims, No Drawings

TRICYCLIC AMINOALKYL DERIVATIVES

This is a continuation of application Ser. No. 646,170 filed June 15, 1967, now abandoned.

The present invention relates to new tricyclic aminoalkyl derivatives and the methods for the preparation and use thereof.

The new tricyclic aminoalkyl derivatives of the present invention are compounds of the formula:

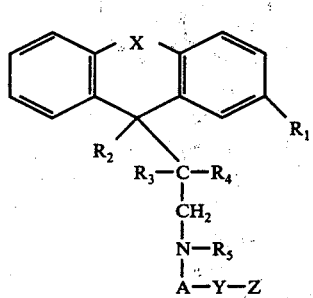
(I)

and the salts thereof with pharmacologically acceptable acids, wherein X is an oxygen or a sulfur atom, a saturated or unsaturated, straight chain or branched alkylene group containing up to 3 carbon atoms, an oxymethylene, thiamethylene or thiaethylene group or a valency bond, $R_1$ is hydrogen, halogen, alkyl, alkoxy or trifluoromethyl, $R_2$ is hydrogen or hydroxyl, $R_3$ is hydrogen or together with $R_2$ represents a further valency bond, $R_4$ and $R_5$ which may be the same or different, are each hydrogen or lower alkyl, A is alkylene which is substituted by an optionally acylated hydroxyl group, Y is an oxygen or sulfur atom or an optionally alkylated imino group and Z is aryl, aralkyl, cycloalkyl or cycloalkylalkyl which may be substituted by halogen, hydroxyl, nitro, amino, alkoxy, aralkoxy, alkyl, trifluoromethyl, alkylamino or alkylsulfonyl groups.

The new compounds according to the present invention possess valuable cardiac and circulatory activities.

The new compounds according to the present invention can be prepared by the conventional methods as, for example, set out hereinafter:

a. reacting an amine of the formula:

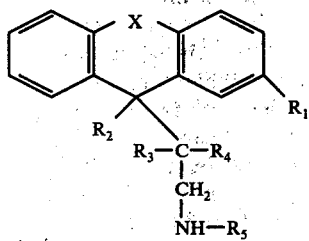
(II)

in which $R_1$, $R_2$, $R_3$, $R_4$, $R_5$ and X have the same significances as set out above, with an epoxide of the formula:

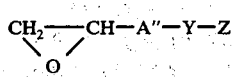
(III)

in which Y and Z have the same significances as set out above and A" represents an alkylene radical which contains two carbon atoms less than A, or with the corresponding halohydrin; or b. condensing an amine of the formula:

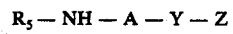
(IV)

in which $R_5$, A, Y and Z have the same significances as set out above, with a compound of the formula:

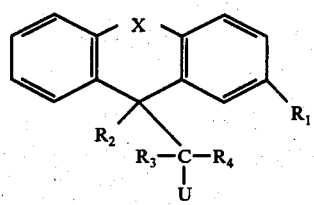
(V)

in which $R_1$, $R_2$, $R_3$, $R_4$ and X have the same significances as set out above and U represents a carbonyl or carboxyl function, and reducing the intermediate thereby obtained. Thereafter, the compound (I), insofar as $R_5$ is a hydrogen atom, is, if desired, then alkylated, in the conventional manner, on the nitrogen atom and, if desired, converted into the corresponding acid-addition salt.

The reaction of compounds (II) and (III) can be brought about by simply heating the reaction components, if desired, in the presence of an inert, high-boiling solvent. When, in place of the epoxides (III), there are used the corresponding halohydrins, then it is advantageous to add a base, for example, an excess of the amine (II), for combination with the hydrogen halide split off in the reaction.

The compounds (V) are either aldehydes having the formula:

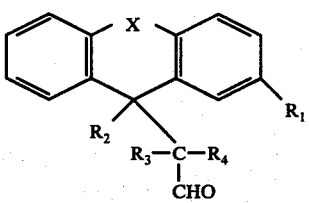
(Va)

in which $R_1$, $R_2$, $R_3$, $R_4$ and X have the same significances as set out above, or reactive derivatives of carboxylic acids of the formula:

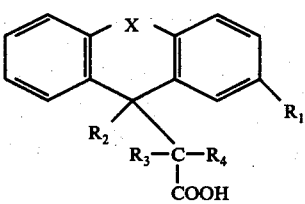
(Vb)

in which $R_1$, $R_2$, $R_3$, $R_4$ and X have the same significances as set out above.

As reactive carboxylic acid derivative, it is preferable to use the acid halide.

The reaction of compounds (IV) and (V) is carried out by heating in an inert solvent, preferably with the addition of a suitable condensation agent, i.e., care is taken, in the usual manner, that water split off during the reaction is removed or bases, such as an excess of the amine (IV), are added for combining with the hydrogen halide split off.

The azomethine or acid amide obtained in the first stage of process (b) is thereafter reduced, in the conventional manner, to compound (I). The reduction is preferably carried out with complex metal hydrides, such as for example, with lithium aluminum hydride or sodium borohydride, or by catalytic hydrogenation. An advantageous variant of the process consists in combining the condensation of compounds (IV) and (Va) with the subsequent reduction i.e., the carbonyl compound is reduced in the presence of the amine.

The following N-alkylation of the products having the formula (I), when $R_5$ is a hydrogen atom, can be carried out in the usual manner, for example, by catalytic hydrogenation in the presence of a suitable aldehyde, by acylation and subsequent reduction by means of complex metal hydrides or by reaction with a suitable alkyl halide.

The basic compounds according to the present invention can be converted, in the conventional manner, into the corresponding addition salts using therefor an organic or inorganic acid. As examples of suitable inorganic acids, there may be mentioned hydrogen halides, sulfuric acid, and phosphoric acid and, as examples of organic acids, there may be mentioned acetic acid, lactic acid, maleic acid, tartaric acid, citric acid and oxalic acid.

The amines of formula (II) required as starting materials can be prepared by the procedure described in German patent application No. B 86165 IVb/12o by reducing in a known manner, compounds of the general formula

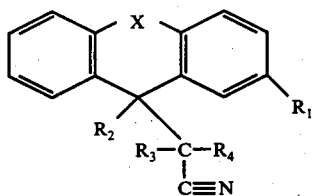

(XIII)

in which $R_1$, $R_2$, $R_3$, $R_4$ and X have the same significances as set out above and the compounds obtained of the general formula II, in the case in which $R_2$ is a hydroxyl group, then, if desired, subsequently dehydrated or, in the case in which $R_2$ and $R_3$ represent an additional valency bond, then, if desired, subsequently hydrogenated. In the case in which in the substances of formula II, $R_5$ is a lower alkyl group, this can be introduced by N-alkylation in the usual way, for example, by catalytic hydrogenation in the presence of a suitable aldehyde, by acylation and subsequent reduction using complex metal hydrides or by reaction with an appropriate alkyl halide.

The nitriles XIIIa of the formula

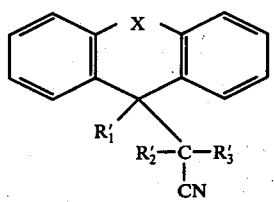

(XIIIa)

wherein $R_1'$ is hydrogen, or the hydroxyl group, $R_2'$ is hydrogen whereby $R_1'$ and $R_2'$ together can also represent a double bond, $R_3'$ is hydrogen or a lower alkyl group, and X is oxygen, sulfur, a saturated or unsaturated, straight or branched alkylene group with 2 to 3 carbon atoms, the oxymethylene, thiamethylene, thiaethylene, carbonyl group or a velency bond, used as starting materials are obtained by a type of "aldol condensation" from tricyclic ketones of the general formula

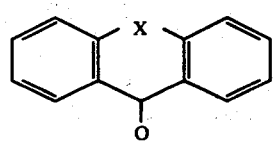

(XIIIb)

in which X has the above-given meaning, with nitriles of the general formula

(XIIIc)

in which $R_3'$ has the above-given meaning, in the presence of a basic condensation agent — preferably lithium amide in liquid ammonia — whereupon, if desired, one subsequently dehydrates the hydroxy-nitriles XIIIa obtained ($R_1'$ = OH; $R_2'$ = H) to the corresponding unsaturated nitriles XIIIa ($R_1'$ and $R_2'$ form a double bond) and can selectively hydrogenate with amalgamated aluminum to the saturated nitriles XIIIa ($R_1'$ = H; $R_2'$ = H).

The reduction, according to the invention, of the nitriles XIIIa to the amines is carried out in the usual manner; for this purpose one preferably uses the complex metal hydrides, such as lithium aluminum hydride, especially when $R_1'$ and $R_2'$ are to form a double bond in the end product. In principle, however, one can also hydrogenate catalytically, whereby, in the case in which X signifies a carbonyl group, a pressureless hydrogenation, for example, with Raney nickel, is even to be preferred.

Since the hydrogenation can be carried out selectively, in general, one will start from a nitrile in which $R_1'$ and $R_2'$ already have the significance desired in the end product. However, for the preparation of amines in which $R_1'$ and $R_2'$ signify hydrogen, it is also quite possible also to start from the unsaturated nitriles XIIIa ($R_1'$ and $R_2'$ form a double bond) and, in one or two steps, to hydrogenate these twice, namely, not only at the double bond but also at the nitrile group. Since the C=C double bond, is, in general, not or only slowly attacked by complex metal hydrides, such as lithium aluminum hydride, it is recommended, in such cases, to hydrogenate catalytically, at the same time, in one step. When, as end products, these tricyclic ethylamines are to be prepared in which $R_1'$ and $R_2'$ either both represent hydrogen atoms or together a double bond, one can also start from hydroxy-nitriles XIIIa ($R_1'$ = OH) and thereafter, by splitting off water and, if desired, subsequently hydrogenating the double bond, get the desired end products.

In the following Examples, the process is explained in more detail.

EXAMPLES

A. Preparation of compounds of formula II with $R_2$ = OH and $R_3$ = H from compounds XIIIa (Nitriles) with $R_1'$ = OH and $R_2'$ = H.

EXAMPLE 1

9-hydroxy-9-(2-aminoethyl)-thiaxanthene 18.5 g. 9-hydroxy-9-cyanomethyl-thiaxanthene (0.07 mol) are substantially dissolved in 150 ml. ether and slowly added dropwise, with stirring and external cooling, to a suspension of 3.8 g. lithium aluminum hydride (0.1 mol) in 50 ml. ether. The reaction mixture is subsequently vigorously stirred for 2 hours at room temperature and carefully decomposed by the addition of saturated, aqueous sodium chloride solution. The precipitated precipitates of the metal hydroxides agglomerate and, in this form, can be filtered off with suction. The filter cake is thoroughly washed through with ether and from the combined ethereal filtrates one obtains, after drying with potassium carbonate, 9-hydroxy-9-(2-aminoethyl)-thiaxanthene in the form of the hydrochloride by the dropwise addition of ethereal hydrochloric acid. The yield amounts to 17.0 g. (82% of theory) of m.p. 180°. After recrystallisation from isopropanol, the yield drops to 12.5 g. (61% of theory); the melting point thereby increases to 188°.

EXAMPLE 2

5-hydroxy-5-(2-aminoethyl)-10,11-dihydro-5H-dibenzo-[a,d]-cycloheptene 7 g. 5-hydroxy-5-cyanomethyl-10,11-dihydro-5H-dibenzo-[a,d]-dycloheptene (0.028 mol) are dissolved in 50 ml. absolute ether and added dropwise to a suspension of 1.12 g. lithium aluminium hydride (0.028 mol) in 25 ml. ether. After a reaction time of two hours at room temperature, the reaction mixture is decomposed with cooking salt solution analogously to Example 1 and worked up. One thus obtains 6.2 g. (87.5% of theory) of a crude base from which one precipitates the hydrochloride in ethereal solution. The amorphous salt melts between 101° and 110° and is again converted into the free base with 2N sodium hydroxide solution. One extracts with ether, evaporates off the ether, recrystallises from petroleum ether with a boiling range of 100° - 140° and thus obtains 4.6 g. (64.9% of theory) of crystals of melting point 113° - 114°.

EXAMPLES 3 - 19

In a manner analogous to that described in Example 1 or 2, one obtains the following compounds, whereby the reaction conditions given in Table I are used.

Not only in Table I but also in all the other Tables, the following abbreviations are uniformly used:

B = benzene
Benz = benzine of boiling range 53° - 73°
PF = petroleum fraction of boiling range 100° - 140°
Isopr = isopropanol
A = alcohol
Hex = hexane
Ae = ether
THF = tetrahydrofuran
acetic ester = acetic acid ethyl ester
RT = room temperature
Rfl = reflux boiling

TABLE I

| compound | solvent | reaction time in hours | nitrile mol | LiAlH₄ mol | temp. | m.p. of base | m.p. of hydrochloride | yield |
|---|---|---|---|---|---|---|---|---|
| 9-hydroxy-9-(2-aminoethyl-1)-fluorene | Ae | 2 | 0.1 | 0.1 | RT | 114° | — | 52% |
| 9-hydroxy-9-(2-aminoethyl-1)-thiaxanthene | Ae | 2 | 0.07 | 0.1 | RT | — | 188–189° (isopr) | 82% m.p. 180° 61% m.p. 188 |
| 5-hydroxy-5-(2-aminoethyl-1)-10,11-dihydro-5d-dibenzo-[a,d]-cycloheptene | Ae | 2 | 0.028 | 0.028 | RT | 113–114° (FF) | — | 87.5% crude, 64.9% |
| 5-hydroxy-5-(2-aminoethyl-1)-5H-dibenzo-[a,d]-cycloheptene | THF | 2 | 0.1 | 0.15 | RT | 156–158° | — | 82% |
| 11-hydroxy-11-(2-aminoethyl-1)-6,11-dihydro-dibenzo-[b,e]-oxepine | Ae + THF | 2 | 0.4 | 0.44 | RT | — | 110–115° | 69% (HCl) |
| 11-hydroxy-11-(2-aminoethyl-1)-6,11-dihydro-dibenzo-[b,e]-thiepine | Ae + THF | 2 | 0.055 | 0.1 | 0.5° | 118–119° | 113–115° | 58% (HCl) |
| 12-hydroxy-12-(2-aminoethyl-1)-5,6,7,12-tetrahydro-dibenzo-[a,d]-cyclooctene | Ae + THF | 1 | 0.086 | 0.12 | 38–40° | — | 190–200° | 44% (HCl) |
| 12-hydroxy-12-(2-aminoethyl-1)-7,12-dihydro-6H-dibenzo-[b,e]-thiocine | Ae + THF | 2 | 0.075 | 0.1 | RT | — | 208° | 50% |
| 10-hydroxy-10-(2-aminoethyl)-1)-anthrone | A/H₂ Raney Ni | 5 | 0.056 | 2.5 g Raney Ni | 40–50° | — | 184–185° | 68.5% (HCl) |
| 9-hydroxy-9-(1-aminobutyl | Ae | 2 | 0.102 | 0.15 | Rfl | — | 215° | 83.5% |

TABLE I-continued

| compound | solvent | reaction time in hours | nitrile mol | LiAlH$_4$ mol | temp. | m.p. of base | m.p. of hydro-chloride | yield |
|---|---|---|---|---|---|---|---|---|
| 2)-fluorene | | | | | | | | |
| 9-hydroxy-9-(1-aminobutyl-2)-xanthene | Ae | 1 | 0.127 | 0.191 | Rfl | 134–135° | — | 79.5% |
| 9-hydroxy-9-(1-amino-butyl-2)-thiaxanthene | Ae | 1 | 0.1 | 0.15 | Rfl | — | 204–205° | 81.5% |
| 5-hydroxy-5-(1-aminobutyl-2)-10,11-dihydro-5H-dibenzo-[a,d]-cyclo-heptene | Ae | 2 | 0.0415 | 0.06 | RT | — | 166–167° | 56.7% |
| 5-hydroxy-5-(1-aminobutyl-2)-5H-dibenzo-[a,d]-cycloheptene | Ae/THF | 1 | 0.1 | 0.15 | Rfl | 139–140° | 294° (dec.) | 70.4% |
| 11-hydroxy-11-(1-aminobutyl-2)-6,11-dihydro-dibenzo-[b,e]-oxepine | Ae/THF | 2 | 0.072 | 0.105 | 10° | — | 227–228° | 69.5% |
| 11-hydroxy-11-(1-aminobutyl-2)-6,11-dihydro-dibenzo-[b,e]-thiepine | Ael THF | 2 | 0.112 | 0.16 | RT | — | 253° | 54% |
| 12-hydroxy-12-(1-aminobutyl-2)-5,6,7,12-tetra-hydro-dibenzo-[a,d]-cyclo-octene | Ae | 1 | 0.0276 | 0.04 | Rfl | — | 249–250° | — |

The nitriles XIIIa with $R_1' =$ OH and $R_2' =$ H, used as starting materials, are prepared in the following ways:

Variant a:

5-hydroxy-5-cyanomethyl-10,11-dihydro-5H-dibenzo-[a,d]cycloheptene, with the use of sodamide in liquid ammonia.

In a three-necked flask, which is provided with a dry ice/methanol reflux cooler, ground-in stirrer and dropping funnel, there is prepared a sodamide solution by the addition of 2.3 g. sodium (0.1 mol) and a few particles of iron (III) nitrate to 100 ml. liquid ammonia. After the complete disappearance of the blue colour, 3.08 g. acetonitrile (0.075 mol) are quickly added dropwise and, immediately thereafter, mixed portionwise with 10.4 g. 10,11-dihydro-5H-dibenzo-[a,d]-cycloheptene-5-one (dibenzo-suberone) (0.05 mol). The reaction mixture is stirred for 2 hours at the reflux temperature of the boiling ammonia. The sodium compound of the 5-hydroxy-5-cyanomethyl compound formed in this way is subsequently decomposed by the addition of 6.4 g. ammonium chloride (0.12 mol). After the removal of the dry ice cooler and addition of 80 ml. ether, one allows the ammonia to evaporate off overnight. One filters off inorganic material with suction and evaporates the ethereal solution. The residue (8.1 g. = 6.45% of theory) still contains small amounts of starting substance. By reprecipitation from ether/benzine, the desired product is isolated in pure form. The yield amounts to 4.5 g. (36% of theory). M.p. 120°–122°.

Variant b:

5-hydroxy-5-cyanomethyl-10,11-dihydro-5H-dibenzo-[a,d]-cycloheptene, with the use of lithium amide in liquid ammonia.

Analogously to Variant (a), a lithium amide solution is prepared in a three-necked flask from 1.38 g. lithium (0.2 mol) in 200 ml. ammonia. Subsequently, a solution of 20.8 g. dibenzo-suberone (0.1 mol) and 8.2 g. acetonitrile in 40 ml. ether is added dropwise. After a reaction time of 2 hours, 24.0 g. ammonium chloride are introduced. One allows the ammonia to evaporate overnight from the open flask. After the addition of further ether and filtering off the inorganic material with suction, one obtains, as evaporation residue of the ethereal solution, 23.7 g. of crude product from which, by reprecipitation according to Variant a, 18.5 g. pure substance are isolated (m.p. 120°–121° ).

In analogous manner, one obtains the following nitriles XIIIa with $R_1'$ = OH and $R_2'$ and $R_2'$ = H, used as starting materials, whereby the reaction conditions given in Table II are used:

TABLE II

| compound | ketone (mol) | nitrile (Mol) | metal amide (mol) | ammonia (mol) | m.p. ° C. | solvent | yield crude | yield pure |
|---|---|---|---|---|---|---|---|---|
| 9-hydroxy-9-cyanomethyl-fluorene | 0.15 | 0.225 | 0.3 Na | 300 | 110–111 | benz | 96% | 65% |
| 9-hydroxy-9-cyanomethyl-xanthene | 0.2 | 0.4 | 0.4 Li | 750 | 137–138 | benz | 91% | 73% |
| 9-hydroxy-9-cyanomethyl-thiaxanthene | 0.3 | 0.6 | 0.6 Li | 1200 | 127–128 | PF | — | 77% |
| 5-hydroxy-5-cyanomethyl- | | | | | | | | |

TABLE II-continued

| compound | ketone (mol) | nitrile (Mol) | metal amide (mol) | ammonia (mol) | m.p. °C. | solvent | yield crude | yield pure |
|---|---|---|---|---|---|---|---|---|
| 10,11-dihydro-5H-dibenzo-[a,d]-cycloheptene 5-hydroxy-5-cyanomethyl- | 0.05 | 0.075 | 0.1 Na | 100 | 120–122 | Ae/benz | about 64% | 36% |
| 10,11-dihydro-5H-dibenzo-[a,d]-cycloheptene 5-hydroxy-5-cyanomethyl- | 0.1 | 0.2 | 0.2 Li | 200 | 121–122 | B and Isopr | — | 75% |
| 10,11-dihydro-5H-dibenzo-[a,d]-cycloheptene 5-hydroxy-5-cyanomethyl- | 0.2 | 0.4 | 0.4 Li | 400 | 202–204 | A | 90% | 73% |
| 11-hydroxy-11-cyanomethyl-6,11-dihydro-dibenzo-[b,e]-oxepine | 0.2 | 0.4 | 0.4 Li | 500 | 147–148 | B | — | 90.5% |
| 11-hydroxy-11-cyanomethyl-6,11-dihydro-dibenzo-[b,e]-thiepine | 0.05 | 0.1 | 0.1 Li | 150 | 119–120 | B/hex | 87% | 53% |
| 12-hydroxy-12 cyanomethyl-5,6,7,12-tetra-hydro-dibenzo-[a,d]-cyclo-octene | 0.1 | 0.1 | 0.1 Li | 500 | 161–163 | Isopr | 66.5% | 46% |
| 12-hydroxy-12-cyanomethyl 7,12-dihydro-6H-dibenzo-[b,e]-thiocine | 0.1 | 0.1 | 0.1 Li | 300 | 143–145 | A | 57.5% | — |
| 10-hydroxy-10-cyanomethyl-anthrone | 0.15 | 0.3 | 0.3 Na | 750 | 170–171 | Isopr | — | 64.5% |
| 9-hydroxy-9-(1-cyanopropyl-1)-fluorene | 0.15 | 0.3 | 0.3 Na | 300 | 133–135 | PF | 95% | 83% |
| 9-hydroxy-9-(1-cyanopropyl-1)-fluorene | 0.15 | 0.3 | 0.3 Li | 500 | 133 | — | 92% | — |
| 9-hydroxy-9-(1-cyanopropyl-1)-xanthene | 0.15 | 0.225 | 0.3 Li | 500 | 106–107 | PF | ~100% | — |
| 9-hydroxy-9-(1-cyanopropyl-1)-thiaxanthene | 0.15 | 0.3 | 0.3 Li | 500 | 103–104 | Isopr | 95% | — |
| 5-hydroxy-5-(1-cyanopropyl-1)-10,11-dihydro-5H-dibenzo-[a,d]-cycloheptene | 0.15 | 0.3 | 0.3 Li | 300 | 141–142 | Isopr | ~100% | 72.3% |
| 5-hydroxy-5-(1-(cyanopropyl-1)-5H-dibenzo-[a,d]-cycloheptene | 0.15 | 0.3 | 0.3 Li | 400 | 161–162 | A | 92% | — |
| 11-hydroxy-11-(1-cyanopropyl-1)-6,11-dihydro-dibenzo-[b,e]-oxepine | 0.1 | 0.2 | 0.2 Li | 300 | 158–159 | B | 95% | 65% |
| 11-hydroxy-11-(1-cyanopropyl-1)-6,11-dihydro-dibenzo-[a,d]-thiepine | 0.15 | 0.3 | 0.3 Li | 500 | — | — | — | — |
| 12-hydroxy-12-(1-cyanopropyl-1) fluorene | 0.15 | 0.3 | 0.3 Li | 300 | 115–116 | Isopr | — | 36% |

B. Preparation of compounds of formula II in which $R_2$ and $R_3$ together form a double bond from compounds II with $R_2$ = CH and $R_3$ = H by subsequent dehydration.

EXAMPLE 20

11-(1-aminobutylidene-2)-6,11-dihydro-dibenzo-[b,e]-oxepine (Variant 1)

12 g. 11-hydroxy-11-(1-aminobutyl-2)-6,11-dihydro-dibenzo-[b,e]-oxepine/hydrochloride (0.0376 mol) prepared according to A, in 50 ml. alcohol which is saturated at room temperature with dry hydrogen chloride, are heated to the boil for 1 hour. After cooling, there crystallise out 6.8 g. of the analytically pure hydrochloride of 11-(1-aminobutylidene-2)-6,11-dihydro-dibenzo-[b,e]-oxepine of m.p. 223°–224°. A further 3 g. of the desired product are isolated from the mother liquor by partial evaporation and subsequent recrystallisation from isopropanol. The total yield amounts to 86.7% of theory.

EXAMPLE 21

5-(1-aminobutylidene-2)-dibenzo-[a,d]-cycloheptene. (Variant 2)

11.3 g. 5-hydroxy-5-(1-aminobutyl-2)dibenz-[a,d]-cycloheptene (0.0405 mol), prepared according to A, are dissolved in 100 ml. 48% hydrobromic acid and heated for 1 hour on a boiling water bath. After the addition of excess sodium hydroxide solution, the base is isolated by ether extraction and purified by high vacuum distillation. The yield amounts of 7.2 g. of a pale, yellowish oil (68% of theory) of boiling point of 160° – 162°/0.2 mm. The hydrochloride melts at 194°–195° (isopropanol).

EXAMPLES 22 – 35

One obtains the following compounds, in a manner analogous to that described in Example 20 and 21, whereby the reaction conditions given in Table III are used.

C. Preparation of compounds of formula II in which $R_2$ and $R_3$ together form a double bond, from compounds XIIIa in which $R_1'$ and $R_2'$ together form a double bond.

EXAMPLE 36

5-(1-aminobutylidene-2)-10,11-dihydro-5H-dibenzo-[a,d]-cycloheptene.

5.9 g. (1-cyanopropylidene-1)-10,11-dihydro-5H-dibenzo[a,d]-cycloheptene (0.023 mol) are boiled under reflux for 2 hours in ethereal solution (100 ml.) with 1.14 g. lithium aluminium hydride (0.03 mol). After the careful addition of a saturated aqueous cooking salt solution, the precipitated hydroxides are filtered off with suction and, from the dried ethereal solution, the basic components precipitated out as hydrochloride. After a single reprecipitation from alcohol/ether, the yield of the analytically pure products amounts to 4.89 (70.6% of theory) of m.p. 224°–225°.

EXAMPLES 37 – 42

One obtains the following compounds in a manner analogous to that described in Example 36, whereby the reaction conditions given in Table IV are used.

TABLE III

| compound | variant | solvent | reaction time (Hrs.) | temp. | m.p. of hydrochloride | yield |
| --- | --- | --- | --- | --- | --- | --- |
| 9-(1-aminoethylidene)-fluorene | 1 | A/HCl | ½ | Rfl | 268–270° | 60.1% |
| 9-(1-aminoethylidene)-xanthene | 1 | A/HCl | ½ | RT | 175° | 93% |
| 9-(1-aminoethylidene)-thiaxanthene | 1 | A/HCl | 1 | Rfl | 183–184√ | 90.2% |
| 5-(1-aminoethylidene)-10,11-dihydro-5H-dibenzo-[a,d]-cycloheptene | 1 | A/HCl | 1 | Rfl | 208–209° | 59.5% |
| 5-(1-aminoethylidene)-5H-dibenzo-[a,d]-cycloheptene | 1 | A/HCl | 1 | Rfl | 232–233° | 65.5% |
| 11-(1-aminoethylidene-6,11-dihydro-dibenzo-[b,e]-oxepine | 1 | A/HCl | 1 | Rfl | 235–237° | 37.1% |
| 11-(1-aminoethylidene)-6,11-dihydro-dibenzo-[b,e]-thiepine | 1 | A/HCl | 1 | Rfl | 217–218° | 83.0% |
| 12-(1-aminoethylidene)-5,6,7,12-tetrahydro-dibenzo-[a,e]-cyclooctene | 1 | A/HCl | 1 | Rfl | 243–245° | 47.5% |
| 9-(1-aminobutylidene-2)-fluorene | 2 | 48% HBr glacial acetic acid | 2 | 100 | 239° | 91.0% |
| 9-(1-aminobutylidene-2)-thiaxanthene | 1 | A/HCl | 1 | Rfl | 232–233° | 84.0% |
| 5-(1-aminobtuylidene-2)-10,11-dihydro-5H-dibenzo-[a,d]-cycloheptene | 1 | A/HCl | 1 | Rfl | 219–220° | 79.5% |
| 5-(1-aminobutylidene-2)-5H-dibenzo-[a,d]-cycloheptene | 2 | 48% HBr | 1 | 100 | 194–195° | 68% |
| 11-(1-aminobutylidene-2)-6,11-dihydro-dibenzo-[b,e]-oxepine | 1 | A/HCl | 1 | Rfl | 223–224° | 86.7% |
| 11-(1-aminobutylidene-2)-6,11-dihydro-dibenzo-[b,e]-thiepine | 1 | A/HCl | 1 | Rfl | 267° | 93.5% |
| 12-(1-aminobutylidene-2)-5,6,7,12-tetrahydro-dibenzo-[a,d]-cyclooctene | 1 | A/HCl | 1 | Rfl | 271–272° | 78.5% |

TABLE IV

| compound | reaction time (hrs.) | temp. | nitrile (mol) | LiAlH$_4$ (mol) | b.p. of base | m.p. hydro-chloride | yield |
|---|---|---|---|---|---|---|---|
| 5-(1-aminoethyl-idene)-fluorene | 2 | 0–5° | 0.05 | 0.11 | 151–52°/ 0.15 m.m. | 208–210° (Isopr) | 73% |
| 11-(1-aminoethyl-idene)-6,11-dihydro-dibenzo-[b,e]-oxepine | 2 | –10° | 0.05 | 0.11 | — | 235–237° | 56% |
| 9-(1-aminobutyl-idene-2)-xanthene | 2½ | –10° | 0.044 | 0.088 | — | 187–188° | 49% |
| 5-(1-aminobutyl-idene-2)-10,11-dihydro-5H-di-benzo-[a,d]-cycloheptene | 2 | Rfl | 0.0228 | 0.03 | — | 224–225° | 70.6% |
| 5-(1-aminobutyl-idene-2)-5H-di-benzo-[a,d]-cycloheptene | 1 | 40 | 0.02 | 0.026 | 157–160°/ 0.2 m.m. | — | 76.4% |

The nitriles XIIIa in which $R_1'$ and $R_2'$ together form a double bond, used as starting materials, are prepared in the following ways by dehydration of the nitriles XIIIa with $R_1'$ = OH and $R_2'$ = H;

Variant a:
5-cyanomethylene-5H-dibenzo-[a,d]-cycloheptene 10 g. 5-hydroxy-5-cyanomethyl-5H-dibenzo-[a,d]-cycloheptene (0.0405 mol), prepared according to A, are heated to boiling for 1 hour in 150 ml. isopropanol saturated with hydrogen chloride. Subsequently, one evaporates the reaction mixture (residue 9.0 g., m.p. 137° – 138°) and recrystallises the product from a petroleum fraction boiling at 100° – 140°. The analytically pure crystals melt at 143° – 144°, the yield amounts to 7.2 g. (79% of theory).

Variant b: 9-(1-cyanopropylidone-1)-xanthene 13 g. 9-hydroxy-9-(1-cyanopropyl-1)-xanthene (0.049 mol), prepared according to A, are well mixed with 25 g. phosphorus pentoxide and heated at 150° for 1 hour on an oil bath. After the careful addition of 300 ml. water, from the reaction mixture there is extracted with ether 10.5 g. (86.8% of theory) of a slowly crystallising yellow-red oil which is subjected to high vacuum distillation (b.p. 160° – 162°/0.2 mm.Hg.). From 9 g. of this red oil, one obtains, after boiling up with benzine, 7.0 g. (57.8% of theory) of analytically pure 9-(1-cyanopropylidene) xanthene of m.p. 82° – 83°.

Variant c:
12-cyanomethylene-5,6,7,12-tetrahydro-[a,d]-cyclooctene 14.8 g. 12-hydroxy-12-cyanomethyl-5,6,7,12-tetrahydro-[a,d]-cyclooctene, prepared according to A, are, as crude product (86% of the calculated nitrogen value), dissolved in 100 ml. alcoholic hydrochloric acid, boiled for one hour under reflux and, after evaporation, subjected to a high vacuum distillation. The first runnings consist mainly of 5,6,7,12-tetrahydro-dibenzo-[a,d]-cyclooctene-12-one (4.5 g.; b.p. 173° – 178°/0.8 mm.Hg.); while the main fraction of 7.5 g. (63% of theory; b.p. 182° – 183°/0.8 mm.Hg.) consists of the desired product, m.p. 64° – 65° C (benzine).

One obtains the following nitriles XIIIa used as starting materials, in which $R_1'$ and $R_2'$ together form a double bond, whereby the reaction conditions given in Table V are used.

TABLE V

| compound | dehydration agent | reaction time (hrs.) | temp. ° C. | b.p. | m.p. ° C. | yield |
|---|---|---|---|---|---|---|
| 9-cyanomethylene-fluorene | P$_2$O$_5$ | ½ | 160 | 155–164°/ 0.05 mm. | 110–111 | 78.1% |
| 9-cyanomethylene-xanthene | A/HCl | 1 | Rfl | 196–200°/ 0.4 mm. | 134–135 | 87.4% |
| 9-cyanomethylene-thiaxanthene | A/HCl | 1 | Rfl | — | 156–158 | 91.1% |
| 5-cyanomethylene-10,11-dihydro-5H-dibenzo-[a,d]-cycloheptene | A/HCl | 1 | Rfl | — | 105–106 | 81.0% |
| 5-cyanomethylene-5H-dibenzo-[a,d]-cycloheptene | Isopr HCl | 1 | Rfl | — | 143–144 | 79.5% |
| 11-cyanomethylene-6,11-dihydro-dibenzo-[b,e]-oxepine | A/HCl | 1 | Rfl | — | 150–151 | 67.6% |
| 11-cyanomethylene-6,11-dihydro-dibenzo-[a,e]-thiepine | A/HCl | 1 | Rfl | — | 176–177 | 83.5% |
| 12-cyanomethylene-5,6,7,12-tetrahydro-dibenzo-[a,d]-cyclooctene | A/HCl | 1 | Rfl | 182–183° 0.8 mm. | 64–65 | 63.5% |
| 10-cyanomethylene-anthrene | oxalic acid | 20 min. | 140° | — | 191–192 | 60.0% |
| 9-(1-cyanopropyl-idene-1)-fluorene | P$_2$O$_5$ | ½ | 150° | 170–171°/ 0.1 mm. | 77–78 | 92.0% |

TABLE V-continued

| compound | dehydration agent | reaction time (hrs.) | temp. ° C. | b.p. ° C. | m.p. ° C. | yield |
|---|---|---|---|---|---|---|
| 9-(1-cyanopropyl-idene-1)-xanthene | $P_2O_5$ | 1 | 150° | 160°/0.2 mm | 82–83 | 86.8% (crude product) |
| 9-(1-cyanopropyl-idene-1)-xanthene | A/HCl | 1 | Rfl | 170–175°/0.1 mm. | 79–80 | 80.5% |
| 9-(1-cyanopropyl-idene-1)-thia-xanthene | A/HCl | 1 | Rfl | — | 106–107 | 85.5% |
| 5-(1-cyanopropyl-idene-1)-10,11-di-hydro-5H-dibenzo-[a,d]-cycloheptene | A/HCl | 1 | Rfl | 173–185°/0.1 mm. | 86–88 | 89.5% |
| 5-(1-cyanopropyl-idene-1)-5H-dibenzo-[a,d]-cycloheptene | $P_2O_5$ | 1 | 160–170° | — | 141–142 | 74.5% |
| 11-(1-cyanopropyl-idene-1)-6,11-dihydro-dibenzo-[b,e]-oxapine | A/HCl | 1 | Rfl | — | 126–127 | 73.5% |
| 11-(1-cyanopropyl-idene-1)-6,11-dihydro-dibenzo-[b,e]-thiepine | A/HCl | ½ | Rfl | — | 112–113 | 62.5% |

D. Preparation of compounds of formula II with $R_2 =$ H and $R_3 =$ H from compounds XIIIa (nitriles) with $R_1' =$ H and $R_2' =$ H.

EXAMPLE 43

11-(1-aminobutyl)-2)-6,11-dihydro-dibenzo-[b,e]-oxepine 17.5 g. 11-(1-cyanopropyl-1)-6,11-dihydro-dibenzo-[b,e]-oxepine (0.0667 mol) in 150 ml. ether are added dropwise at 0° – 5° C., with good stirring, to a suspension of 3.8 g. lithium aluminium hydride in ether (0.1 mol). After a reaction time of two hours, one decomposes the reaction mixture at 5 to 10° by the addition of saturated aqueous cooking salt solution, filters off the separated hydroxides with suction and precipitates from the dried ethereal solution, by the addition of ethereal hydrochloric acid, the basic components as hydrochloride. After recrystallisation from isopropanol, one obtains 17.5 g. 11-(1-aminobutyl-2)-6,11-dihydro-dibenzo-[b,e]-oxepine (87% of theory) as hydrochloride; m.p. 219° – 220°.

EXAMPLE 44

9-(2-aminoethyl)-xanthene

After the addition of 2 g. platinum oxide; 45 g. (0.21 mol) 9-cyanomethyl-xanthene in a mixture of 500 ml. glacial acetic acid and 5 ml. concentrated sulphuric acid are catalytically hydrogenated for 4 hours without the use of pressure. Subsequently, the acetic acid is substantially removed by evaporation in a vacuum (about ¾ of the volume). The residue is taken up in water and the neutral products are removed by extraction with ether. The basic products are then liberated by the addition of 2N sodium hydroxide solution and isolated by extraction with ether. The evaporation residue of the ethereal solution gives, after high vacuum distillation, 28.4 g. (60% of theory) 9-(2-aminoethyl)-xanthene of b.p. 145° – 148° C./0.5 mm.Hg.

EXAMPLE 45

9-(1-aminiobutyl-2)-xanthene 22 g. 9-(1-cyanopropyl-1)-xanthene (0.0885 mol) are reduced by heating under reflux for two hours in 350 ml. absolute ether with 5.05 g. lithium aluminium hydride (0.133 mol). Thereafter one decomposes with cooking salt solution and subsequently isolates from the filtered ethereal solution, by immediate precipitation 25.5 g. (98% of theory) of the desired hydrochloride of m.p. 251° – 252°.

EXAMPLES 46 – 57

One obtains the following compounds in a manner analogous to that described in Examples 43 to 45, whereby the reaction conditions given in Table VI are used.

TABLE VI

| compound | reaction time (hrs.) | temp. ° C. | solvent | nitrile (mol) | reduction agent | b.p. ° C. | m.p. salt | yield % |
|---|---|---|---|---|---|---|---|---|
| 9-(2-aminoethyl-1)-fluorene | 32 | RT | A | 0.1 | 5 g. RaNi/$H_2$ | 131–135 0.2 mm. | 233–234° HCl | 82.5% |
| 9-(2-aminoethyl-1)-xanthene | 1 | Rfl | THF/Ae | 0.05 | 0.075 mol LiAlH$_4$ | — | 166–167° maleate | 57.5% |
| 9-(2-aminoethyl-1)-xanthene | 4 | RT | glacial acetic acid (1 $H_2SO_4$) | 0.21 | 2 g. PtO$_2$/H$_2$ | 145–148° 0.5 mm. | — | 60.6% |
| 9-(2-aminoethyl-1)-thiaxanthene | 2 | Rfl | THF/Ae | 0.154 | 0.24 mol LiAlH$_4$ | 160–180° 162°/0.3 mm | 78% maleate | |
| 5-(2-aminoethyl-1)-10,11-dihydro-5H-dibenzo-[a,d]-cyclo-heptene | 2 | Rfl | Ae | 0.095 | 0.143 mol LiAlH$_4$ | 148–149°/0.1 mm. | 237–238° HCl | 84.0% |
| 5-(2-aminoethyl)-5H- | 1 | 35 | THF/ | 0.025 | 0.035 | — | 238– | 80.0% |

TABLE VI-continued

| compound | reaction time (hrs.) | temp. °C. | solvent | nitrile (mol) | reduction agent | b.p. °C. | m.p. salt | yield % |
|---|---|---|---|---|---|---|---|---|
| dibenzo-[a,d]-cycloheptene | | | Ae | | mol LiAlH$_4$ | | 240° HCl | |
| 5-(2-aminoethyl-1)-6,11-dihydro-5H-dibenzo-[b,e]-oxepine | 3 | 0-10 | THF/ Ae | 0.0426 | 0.086 mol LiAlH$_4$ | 163-164/ 0.3 mm. | 156° maleate | 81.0% |
| 11-(2-aminoethyl-1)-6,11-dihydro-dibenzo-[b,e]-thiepine | 1 | RT | THF/ Ae | 0.3 | 0.45 mol LiAlH$_4$ | — | 251-252° HCl | 67% |
| 9-(1-aminobutyl-2)-fluorine | 2 | Rfl | Ae | 0.056 | 0.084 mol LiAlH$_4$ | — | 242-243° HCl | 73% |
| 9-(1-aminobutyl-2)-xanthene | 2 | Rfl | Ae | 0.0885 | 0.133 mol LiAlH$_4$ | — | 251-252 HCl | 98.0% |
| 9-(1-aminobutyl-2)-thiaxanthene | 2 | Rfl | Ae | 0.1 | 0.15 mol LiAlH$_4$ | HCl | 243-244 | 89.0% |
| 11-(1-aminobutyl-2)- | 2 | +10° C | Ae | 0.0667 | 0.1 mol LiAlH$_4$ | — | 219-220 HCl | 87% |

The nitriles XIIIa used as starting materials with $R_1' = H$ and $R_2' = H$ are obtained in the following way from nitriles XIIIa in which $R_1'$ and $R_2'$ together form a double bond.

11-(cyanomethyl)-6,11-dihydro-dibenzo-[b,e]-oxepine

A saturated mercury II chloride solution is prepared in 150 ml. dry ether. After the addition of 12 g. aluminium fillings, one leaves the solution to stand for 3 – 5 minutes and, after shaking up twice, decants. The aluminium amalgamated in this manner is now washed several times with absolute ether and finally covered with 300 ml. ether in a stirring apparatus. Subsequently, one mixes with 12 g. 11-(cyanomethylene)-6,11-dihydro-dibenzo-[b,e]-oxepine (0.051 mol), prepared according to C, and adds 12 ml. water thereto in the course of 5 hours, with vigorous stirring. The reaction mixture is then left to stand overnight. The inorganic components are filtered off with suction, the filtrate evaporated in a vacuum and one obtains 11.5 g. (95.5% of theory) of practically pure reduction product of m.p. 85° – 86°. After recrystallising once from a petroleum fraction of m.p. 100° – 140° C., the melting point increases to 87° – 89°. The UV-spectrum shows the absence of the cross-conjugated double bond.

In analogous manner, one obtains the following nitriles XIII used as starting materials with $R_1' = H$ and $R_2' = H$ (Table VII).

TABLE VII

| compound | m.p. | solvent | yield |
|---|---|---|---|
| 9-cyanomethyl-fluorene | 134-135° | acetic ester | 92% |
| 9-cyanomethyl-xanthene | 140-141 | Isopr | 94.2% |
| 9-cyanomethyl-thiaxanthene | 72-73 | PF | 91% |
| 5-cyanomethyl-10,11-dihydro-5H-dibenzo-[a,d]-cycloheptene | 91-92 | Isopr | 88.0% |
| 5-cyanomethyl-5H-dibenzo-[a,d]-cycloheptene | 102-103 | PF | 89.0% |
| 11-cyanomethyl-6,11-dihydro-dibenzo-[b,e]-oxepine | 87-89 | PF | 95.5% |
| 11-cyanomethyl-6,11-dihydro-dibenzo-[b,e]-thiepine | 124- | C$_2$H$_5$OH | 94.5% |
| 9-(1-cyanopropyl-1)-fluorene | 81-82 | Isopr | 69.5% |
| 9-(1-cyanopropyl-1)-xanthene | 113-114 | benzine | 72.0% |
| 9-(1-cyanopropyl-1)-thioxanthene | 101-102 | Isopr | 84.5% |

TABLE VII-continued

| compound | m.p. | solvent | yield |
|---|---|---|---|
| 9-(1-cyanopropyl-1)-6,11-dihydro-dibenzo-[b,e]-oxepine | 165-170/ 0.2* | — | 81.2% |

*b.p. ° C./mm.Hg.

The epoxides having the formula (III) can be prepared, for example, by the reaction of an alkali metal derivative, of the formula:

$$Me - Y - Z \qquad (VI)$$

in which Y and Z have the same significances as set out above, and Me is an alkali metal atom, with a halogen compound of the formula:

$$CH_2\underset{O}{\overset{}{\diagdown}}CH-A''-Hal \qquad (VII)$$

in which A" has the same meaning as given above and Hal is a halogen atom.

Instead of the alkali metal compounds (VI), the free compounds of the formula H—Y—Z can also be used and these compounds condensed with the halogen compounds (VII) in the presence of catalytic amounts of a Lewis acid, preferably boron trifluoride. The halohydrins thus obtained must thereafter be treated with agents for splitting off hydrogen halide and preferably with strong inorganic bases.

The aldehydes of the formula (Va) mentioned above as starting materials can be prepared, for example, by the ethynylation of ketones of the formula:

(VIII)

in which R$_1$ and X have the same significances as set out above, to produce carbinols of the formula:

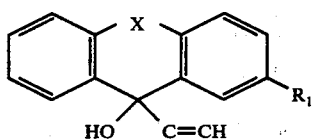

(IX)

in which $R_1$ and X have the same meanings as given above, followed by a Meyer-Schuster reaction. In the aldehydes (Va) obtained in this manner, $R_2$ and $R_3$ together form a further valency bond.

Aldehydes of the formula (Va) in which $R_2$ and $R_3$ both represent hydrogen atoms, can be prepared, under alkaline conditions, by the reaction of cyclic diphenyl-methane derivatives of the structural formula:

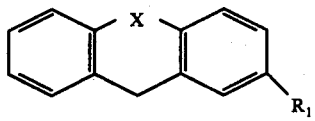

(X)

in which $R_1$ and X have the same significances as set out above, with an acetal of chloroacetaldehyde, with the formation of intermediates of the formula:

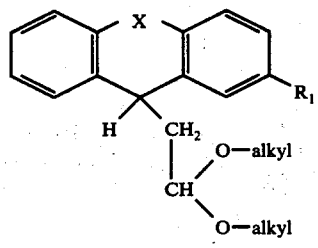

(XI)

in which $R_1$ and X have the same meanings as given above.

The carboxylic acids of the formula (Vb) required as starting materials can be obtained, for example, by the reaction of ketones of the formula (VIII) with a fatty acid ester, for example, tert.-butyl actate, in the presence of an alkaline condensation agent. There are thusly formed, as intermediates, hydroxy esters of the formula:

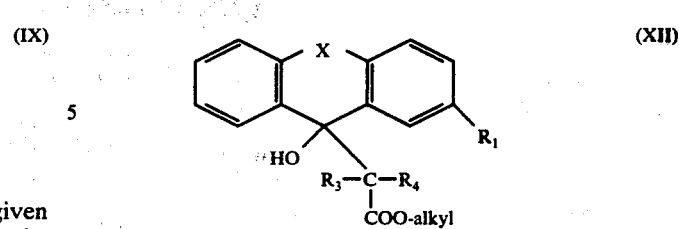

(XII)

in which $R_1$, $R_3$, $R_4$ and X have the same meanings as given above, which, by careful acid hydrolysis, can be converted into the desired carboxylic acids having the formula (Vb) in which $R_2$ is a hydroxyl group. Under vigorous hydrolysis conditions, for example, with glacial acetic acid or 6N hydrochloric acid, there is brought about a splitting off of water and saponification with the formation of carboxylic acids of the formula (Vb) in which $R_2$ and $R_3$ together form a further valency bond. Finally, under anhydrous conditions, for example, with alcoholic hydrochloric acid, a splitting off of water can first be brought about, then the carbon-carbon double bond reduced, for example, with amalgamated aluminum, and finally, under aqueous-acidic reaction conditions, the carboxylic acids having the formula (Vb), in which $R_2$ and $R_3$ both represent hydrogen atoms, produced by saponification.

The following examples are given for the purpose of illustrating the present invention and are in nowise to be construed as a limitation thereof.

EXAMPLE 1

N-[2-(6,11-dihydro-dibenzo-[b,e]-oxepine-11-yl)-ethyl]-1-phenoxy-2-hydroxy-3-amino-propane 12 g. 6,11-dihydro-dibenzo-[b,e]-oxepine-11-yl-ethylamine (0.05 mol) were mixed with 7.82 g. 1-phenoxy-2,3-epoxy-propane (0.0525 mol) and the mixture then heated for 4 hours at 140° C. The reaction mixture was thereafter taken up in ether from which, by the addition of a solution of maleic acid in tetrahydrofuran, there was precipitated out the maleate of N-[2-(6,11-dihydro-dibenzo-[b,e]-oxepine-11-yl]-ethyl]-1-phenoxy-2-hydroxy-3-amino-propane, which could be recrystallized from isopropanol. The yield of the analytically-pure compound amounted to 15.6 g (64% of theory) of compound which had a melting point of 136° – 138° C.

The compounds set out in the following Table I were prepared in an analogous manner:

TABLE I

| COMPOUND | BASE M.P. °C | SALT M.P. °C | YIELD |
|---|---|---|---|
| N-[2-(thiaxanthyl-9)-ethyl]-1-phenoxy-2-hydroxy-3-amino-propane | — | 217° (decomp.) hydrochloride | 61% |
| N-[2-(thiaxanthyl-9)ethyl]-1-(2-chloro-phenoxyy)-2-hydroxy-3-amino-propane | 93—94° | — | 63% |
| N-[2-(thiaxanthyl-9)-ethyl]-1-(3-chloro-phenoxy)-2-hydroxy-3-amino-propane | 94-95° | — | 68% |
| N-[2-(thiaxanthyl-9)-ethyl-1-(3-methyl-phenoxy)-2-hydroxy-3-amino-propane | 80-82° | 160-162° maleate | 65% |
| N-[2-(thiaxanthyl-9)-ethyl-1-(naphthoxy-1)-2-hydroxy-3-amino-propane | — | 165-167° hydrochloride | 69% |
| N-[2-(xanthyl-9)-ethyl]-1-(3-methyl-phenoxy)-2-hydroxy-3-amino-propane | 70-80° | 117-119° maleate | 71% |
| N-[(xanthyl-9)-ethyl]-1-(2-chloro-phenoxy)-2-hydroxy-3-amino-propane | — | 105-110° (amorphous) | 62% |

TABLE I-continued

| COMPOUND | BASE M.P. °C | SALT M.P. °C | YIELD |
|---|---|---|---|
| N-[2-(xanthyl-9)-ethyl]-1-(3-chloro-phenoxy)-2-hydroxy-3-amino-propane | 82–84° | 126–127° maleate | 72% |
| N-[2-(fluorenyl-9)-ethyl]-1-(naphthoxy-1)-2-hydroxy-3-amino-propane | 115–116° | — | 59% |
| N-[2-(xanthyl-9)-ethyl]-1-(naphthoxy-1)-2-hydroxy-3-amino-propane | — | 145–146° maleate | 75% |
| N-[2-(10,11-dihydro-5H-dibenzo-[a,d]-cyclohept-5-enyl)-ethyl]-1-(naphthoxy-1)-2-hydroxy-3-amino-propane | — | 201–203° hydrochloride | 78% |
| N-[2-(6,11-dihydro-dibenzo-[b,e]-oxepine-11-yl)-ethyl]-1-(3-methyl-phenoxy)-2-hydroxy-3-amino-propane | 68–69° | 131–133° maleate | 66% |
| N-[6,11-dihydro-dibenzo-[b,e]-oxepine-11-yl)-ethyl]-1-(3-chloro-phenoxy)-2-hydroxy-3-amino-propane | 78–79° | 136–138° maleate | 67% |
| N-[6,11-dihydro-dibenzo-[b,e]-oxepine-11-yl)-ethyl-1-(2-chloro-phenoxy)-2-hydroxy-3-amino-propane | — | 118–120° maleate | 62% |
| N-[6,11-dihydro-dibenzo[b,e]-oxepine-11-yl)-ethyl]-1-(naphthoxy-1)-2-hydroxy-3-amino-propane | — | 172–173° hydrochloride | 61% |
| N-[2-(6,11-dihydro-dibenzo-[b,e]-oxepine-11-ylidene)-ethyl]-1-phenoxy-2-hydroxy-3-amino-propane | — | 186–187° oxalate | 63% |
| N-[2-(6,11-dihydro-dibenzo-[b,e]-oxepine-11-ylidene)-ethyl]-1-(naphthoxy-1)-2-hydroxy-3-amino-propane | 75° | 189–190° succinate | 66% |
| N-[6,11-dihydro-dibenzo-[b,e]-oxepine-11-yl)-ethyl]-1-cyclehexyloxy-2-hydroxy-3-amino-propane | 64–65° | 106–108° maleate | 79% |
| N-[2-(2-ethyl-6,11-dihydro-dibenzo-[b,e]-oxepine-11-yl)-ethyl]-1-(3-methyl-phenoxy)-2-hydroxy-3-amino-propane | — | 121–122° maleate | 62% |
| N-[6,11-dihydro-dibenzo-[b,e]-oxepine-11-yl)-ethyl]-1-(3-methyl-benzyloxy)-2-hydroxy-3-amino-propane | — | abut 103° (amorphous) | 61% |
| N-[6,11-dihydro-dibenzo-[b,e]-oxepine-11-yl)-ethyl]-1-(4-nitro-phenoxy)-2-hydroxy-3-amino-propane | — | 132° maleate | 71% |
| N-[2-(2-methoxy-6,11-dihydro-dibenzo-[b,e]-oxepine-11-yl)-ethyl]-1-(4-nitro-phenoxy)-2-hydroxy-3-amino-propane | — | 153° oxalate | 86% |
| N-[1-(6,11-dihydro-dibenzo-[b,e]-oxepine-11-1)-butyl-2]-1-phenoxy-2-hydroxy-3-amino-propane | — | abut 98 – 100° (amorphous) | 58% |
| N-[2-(2-methoxy-6,11-dihydro-dibenzo-[b,e]-oxepine-11-yl)-ethyl]-1-phenoxy-2-hydroxy-3-amino-propane | — | 107° maleate | 62% |
| N-[6,11-dihydro-dibenzo-[b,e]-oxepine-11-yl)-ethyl]-1-(2,3-dichloro-phenoxy)-2-hydroxy-3-amino-propane | — | 135–136° maleate | 73% |
| N-[6,11-dihydro-dibenzo[b,e]-oxepine-11-yl)-ethyl]-1-1(2,4-dichlorophenoxy)-2-hydroxy-3-amino-propane | — | 151° maleate | 74% |
| N-[6,11-dihydro-dibenzo[b,e]-oxepine-11-yl)-ethyl]-1-)3,4-dichloro-phenoxy)-2-hydroxy-3-amino-propane | — | 132° maleate | 71% |
| N-[6,11-dihydro-dibenzo[b,e]-oxepine-11-yl)-ethyl]-1-(2,5-dichloro-phenoxy)-2-hydroxy-3-amino-propane | — | 140–141° maleate | 74% |
| N-[2-(2-chloro-6,11-dihydro-dibenzo-[b,e]-oxepine-11-yl-ethyl-1-phenoxy-2-hydroxy-3-amino-propane | 117–119° | 213–214° oxalate | 66% |
| N-[2-(10,11-dihydro-dibenzo-[b,e]-thiepine-11-yl)-ethyl]-1-(naphthoxy-1)-2-hydroxy-3-amino-propane | 143–144° | 169–171° maleate | 59% |
| N-[6,11-dihydro-dibenzo-[b,e]-oxepine-11-yl)-ethyl]-1-benzyl- | — | 130–133° | 63% |

TABLE I-continued

| COMPOUND | BASE M.P. °C | SALT M.P. °C | YIELD |
|---|---|---|---|
| oxy-2-hydroxy-3-amino-propane | | oxalate | |
| N-[6,11-dihydro-dibenzo[b,e]-oxepine-11-yl)-ethyl-1-(2,6-dichloro-phenoxy)-2-hydroxy-3-amino-propane | — | abut 98° (amorphous) maleate | 65% |
| N-[6,11-dihydro-dibenzo[b,e]-oxepine-11-yl]-ethyl]-1-(3-trifluoromethyl-phenoxy)-2-hydroxy-3-amino-propane | — | 124–126° maleate | 72% |
| N-[2-(6,11-dihydro-dibenzo[b,e]-oxepine-11-yl]-ethyl]-1-(4-chloro-phenoxy)-2-hydroxy-3-amino-propane | — | 144–145° maleate | 66% |
| N-[2-(6,11-dihydro-dibenzo-[b,e]-oxepine-11-yl)-ethyl]-1-(4-ethoxy-phenoxy)-2-hydroxy-3-amino-propane | — | 163° maleate | 73% |
| N-[2-(6,11-dihydro-dibenzo-[b,e]-oxepine-11-yl)-ethyl]-1-(cyclopentyloxy)-2-hydroxy-3-amino-propane | — | 121° maleate | 54% |
| N-[2-(6,11-dihydro-dibenzo-[b,e]-oxepine-11-yl)-ethyl]-1-(cycloheptyloxy)-2-hydroxy-3-amino-propane | — | 149° oxalate | 55% |
| N-[2-(6,11-dihydro-dibenzo-[b,e]-oxepine-11-yl)-ethyl]-(cyclooctyloxy)-2-hydroxy-3-amino-propane | — | 168° oxalate | 61% |
| N-[2-(6,11-dihydro-dibenzo-[b,e]-oxepine-11-yl)-ethyl]-1-(cyclohexyl-methoxy)-2-hydroxy-3-amino-propane | — | 169° oxalate | 58% |
| N-[2-(6,11-dihydro-dibenzo-]b,e]-oxepine-11-yl)-ethyl]-1-(3-methyl-cyclohexyloxy)-2-hydroxy-3-amino-propane | — | maleate amorphous | 68% |
| N-[2-(6,11-dihydro-dibenzo-[b,c]-oxepine-11-yl)-ethyl]-1-(2-methyl-phenoxy)-2-hydroxy-3-amino-propane | — | 120–121° maleate | 63% |
| N-[2-(6,11-dihydro-dibenzo-[b,e]-oxepine-11-yl)-ethyl]-1-(4-methyl-phenoxy)-2-hydroxy-3-amino-propane | 69–71° | — | 73% |
| N-[2-(6,11-dihydro-dibenzo-[b,e]-oxepine-11-yl)-ethyl]-1-(4-benzyl-oxy-phenoxy)-2-hydroxy-3-amino-propane | 103-1-5° | – | 69% |
| N-[2-(6,11-dihydro-dibenzo-[b,e]-oxepine-11-yl)-ethyl]-1-(cyclododecyloxy)-2-hyroxy-3-amino-propane | 76–78° | — | 71% |
| N-[2-(6,11-dihydro-dibenzo-[b,e]-oxepine-11-ylidene)-ethyl]-1-(3-methyl-phenoxy)-2-hydroxy-3-amino-propane | — | 150–151° succinate | 58% |
| N-[2-(6,11-dihydro-dibenzo-[b,e]-thiepine-11-ylidene)-ethyl]-1-phenoxy-2-hydroxy-3-amino-propane | — | succinate amorphous | 53% |
| N-[2-(5H-dibenzo-[a,d]-cyclohept-5-enyl)-ethyl]-1-naphthoxy-2-hydroxy-3-amino-propane | 92–93° | 182–184° hydrochloride | 61% |
| N-[2-(11,hydroxy-6,11-dihydro-dibenzo-[b,e]-oxepine-11-yl)-ethyl]-1-phenoxy-2-hydroxy-3-amino-propane | 132–134° | — | 78% |
| N-[2-(6,11-dihydro-dibenzo-[b,c]-oxepine-11-yl)-ethyl]-1-phenylmercapto-2-hydroxy-3-amino-propane | — | 137–138° maleate | 72% |
| N-[2-(2-chloro-thiaxanth-9-ylidene)-ethyl]-1-phenoxy-2-hydroxy-3-amino-propane | 93° | 176–177° maleate | 63% |
| N-[2-(2-chloro-thiaxanthyl-9-ethyl]-1-(3-methyl-phenoxy)-2-hydroxy-3-amino-propane | — | 171–173° maleate | 67% |
| N-[2-(2-chloro-thiaxanthyl-9)-ethyl]-1-phenoxy-2-hydroxy-3-amino-propane | — | 126–128° succinate | 71% |
| N-[ 2-(6,11-dihydro-dibenzo-[b,e]-thiepine-11-yl)-ethyl]-1-phenoxy-2-hydroxy-3-amino-propane | — | hydrochloride amorphous | 61% |
| N-[2-(6,11-dihydro-dibenzo-[b,e]-oxepine-11-yl)-ethyl]-1-(3-nitro-benzyloxy)-2-hydroxy-3-amino-propane | — | 112° oxalate | 81% |
| N-[2-(6,11-dihydro-dibenzo-[b,e]-oxepine-11-yl)-ethyl]-1-(4-methyl-phenylmercapto)-2-hydroxy-3- | — | 133° maleate | 75% |
| N-[2-(6,11-dihydro-dibenzo-[b,e]- | | | |

TABLE I-continued

| COMPOUND | BASE M.P. °C | SALT M.P. °C | YIELD |
|---|---|---|---|
| oxepine-11-yl)-ethyl]-1-(2-methyl-phenylmercapto)-2-hydroxy-3-amino-propane | — | 149° oxalate | 68% |
| N-[2-(6,11-dihydro-dibenzo-[b,e]-oxepine-11-ylidene)-propyl-1]-1-phenoxy-2-hydroxy-3-amino-propane | — | oxalate amorphous | 70% |
| N-[2-(6,11-dihydro-dibenzo-[b,e]-oxepine-11-yl)-ethyl]-1-(3-methyl-phenylmercapto)-2-hydroxy-3-amino-propane | — | 144–145° oxalate | 79% |
| N-methyl-N-[2-(6,11-dihydro-dibenzo-[b,e]-oxepine-11-yl)-ethyl]-1-(3-methyl-phenoxy)-2-hydroxy-3-amino-propane | — | about 90° oxalate | 84% |
| N-[2-(6,11-dihydro-dibenzo-[b,e]-oxepine-11-yl)-propyl-1]-1-(3-methyl-phenoxy)-2-hydroxy-3-amino-propane | — | 167° oxalate | 52% |

The epoxides required as starting material were prepared by one of the following methods:

METHOD A 1 mol of the acidic H compound (H—Y—Z) was heated briefly with 1 mol sodium isopropylate in isopropanol and the sodium compound obtained in this manner boiled for one hour with at least 1 mol epichlorhydrin. The sodium chloride which had separated out was filtered off and the evaporation residue of the filtrate then distilled.

METHOD B 1 mol of the acidic H compound (H—Y—Z) was first mixed with 1 ml. boron trifluoride etherate and then with 1.1 mol epichlorhydrin, thereafter stirred for 2 – 4 hours at 60° C and subsequently distilled. The reaction mixture was then mixed with about two thirds of its weight of powdered sodium hydroxide, boiled in ethereal solution for one hour, filtered with suction, evaporated and the residue distilled.

In the following Table II there are set out the 1-substituted 2,3-epoxy-propanes which were prepared by one of the above-described methods:

EXAMPLE 2

N-[2-(6,11-dihydro-dibenzo-[b,e]-oxepine-11-ylidene)-ethyl]-1-phenoxy-2-hydroxy-3-amino-propane.

11.8 g. 6,11-dihydro-dibenzo-[b,e]-oxepine-11-ylidene-acetaldehyde (0.05 mol) were heated under a water separator with 7.6 g. 1-phenoxy-2-hydroxy-3-amino-propane (0.05 mol) in 75 ml. benzene for one hour. The reaction mixture was thereafter evaporated, the residue taken up with 75 ml. methanol and mixed portionwise with 3.8 g. sodium borohydride (0.1 mol). After boiling under reflux for one hour, the reaction mixture was evaporated and the residue extracted with ether. The ethereal solution which was obtained was dried and a solution of oxalic acid in tetrahydrofuran added thereto which resulted in the precipitation of the oxalate of N-[2-(6,11-dihydro-dibenzo-[b,e]oxepine-11-ylidene)-ethyl]-1-phenoxy-2-hydroxy-3-amino-propane, which could be recrystallized from isopropanol. The yield of the analytically pure product amounted to 13.9 g. (72% of theory) and its melting point was 185° – 187° C.

The 6,11-dihydro-dibenzo-[b,e]-oxepine-11-ylidene-acetaldehyde used as starting material was obtained by the rearrangement of 11-hydroxy-11-ethynyl-6,11-dihydro-dibenzo[b,e]-oxepine (m.p. 93° – 94° C.; obtained by the reaction of 6,11-dihydro-dibenzo-[b,e]-oxepine-11 with acetylene and sodium in liquid ammonia), the rear-

TABLE II

| SUBSTITUENT IN THE 1-POSITION | METHOD | B.P. °C./mm. Hg. | M.P. °C |
|---|---|---|---|
| phenoxy | A | 100–105°/0.1 | — |
| 3-methyl-phenoxy | A | 107–112°/0.6 | — |
| 2-chlorophenoxy | A | 93–100°/0.05 | — |
| 3-chlorophenoxy | A | 120–125°/0.3 | — |
| 4-chlorophenoxy | A | 97–104°/0.05 | — |
| naphthoxy-1 | A | 160–163°/0.3 | — |
| 4-nitro-phenoxy | A | 175–182°/0.4–0.5 | 63–64° |
| 2,6-dimethoxy-phenoxy | A | 135–141°/0.4 | — |
| 2,3-dichlorophenoxy | A | 130–135°/0.4 | 46–47° |
| 2,4-dichlorophenoxy | A | 133–138°/0.2 | — |
| 3,4-dichlorophenoxy | A | 136–141°/0.2–0.3 | — |
| 2,5-dichlorophenoxy | A | 120–130°/0.6 | 59–60° |
| 2,6-dichlorophenoxy | A | 110–115°/0.6 | — |
| 3-trifluoromethyl-phenoxy | A | 80–89°/0.4 | — |
| benzyloxy | B | 125–130°/14 | — |
| 3-methyl-benzyloxy | B | 135–140°/14 | — |
| cyclohexyloxy | B | 90–92°/14 | — |
| cyclopentyloxy | B | 80–84°/14 | — |
| cycloheptyloxy | B | 110–115°/15 | — |
| cyclooctyloxy | B | 126–131°/14 | — |
| 3-methyl-cyclohexyloxy | B | 101–105°/14 | — |
| cyclohexyl-methoxy | B | 110–115°/14 | — | rangement having been carried out in an aqueous alcoholic solution of sulfuric acid with a reaction time of 30 minutes. The compound was obtained in a yield of 82% and had a boiling point of 177° – 179° C./0.6 mm.Hg.

In an analogous manner, there were obtained, in 75% yield, N-[2-(6,11-dihydro-dibenzo-[b,e]-oxepine-11-ylidene)ethyl]-1-(naphthoxy-1)-2-hydroxy-3-amino-propane, the succinate of which had a melting point of 190° – 191° C.

The pharmacological effectiveness of the compounds in accordance with the invention and namely their effectiveness as cardiac and circulatory agents was evaluated by the following procedures:

1. Increase in the heart minute volume

A criterion of the improvement of the blood supply to the organs lies in the increase of the heart minute volume as measured in the aorta of unanesthetized dogs following oral application of an appropriate pharmaceutical.

The tests were carried out on unanesthetized dogs having electromagnetic flowmeters chronically implanted in the aorta ascendens. The mechanical zero line was determined by means of simultaneously chronically implanted sealing flaps or by means of the exact adjustment of an electronic gate of the electro flowmeter. The test compounds were administered to the animal through stomach tubes. All of the compounds were employed dissolved in 10 ml distilled water to which 5% "Lutrol 9"(polyethylene oxide molecular weight — 400) had been added.

The doses employed were not uniform, as in some instances, lower doses were first used and it was further determined whether higher doses would possibly be more effective.

2. β-Receptor Blocking

The cardiac β-receptor blocking activity of a test compound can be evaluated by determination of the inhibition of the anaerobic glycolysis in the myocardium of unanesthetized rats. This latter inhibition is a typical property of β-receptor blocking bio catalysts.

The tests were carried out on Sprague-Dawley rats weighing between about 180 and 220 g. The test compounds were administered intraperitoneally to the rats which had not been anesthetized and who had been fasted for 14 hours. 15 minutes after administration of the test compound the animals were subjected to a deficiency mixture of 5% oxygen and 95% nitrogen, thereafter killed instantly by a blow to the back of the neck. The animal heart was then removed, and the myocardium homogenized. Following conversion of the myocardiac glycogen into glucose, the glucose content was colormetrically determined and the figures recalculated to give the glycogen content. The test compounds were administered in the form of their 1% solutions in 5.5% glucose solution under addition of 10% DMF (dimethylformamide) and 1% gluconic acid. The solutions thusly obtained were diluted with 5.5% glucose solution to a final volume of 1 ml/100 g animal weight and were then administered intraperitoneally.

The doses of test compounds employed was not entirely uniform, for the same reasons as set out above in connection with the first procedure.

The following compounds were employed in the test procedures:

A — N-[(6,11-dihydro-dibenzo-[b,e]-oxepine-11-yl)-ethyl]-1-(2-chlor-phenoxy)-2-hydroxy-3-amino-propane B — N-[2-(thiaxanthyl-9)-ethyl]1-(naphthoxy-1)-2-hydroxy-3-amino-propane C — N-[2-(fluorenyl-9)-ethyl]-1-(naphthoxy-1)-2-hydroxy-3-amino-propane D — N-[2-(6,11-dihydro-dibenzo-[b,e]-oxepine-11-yl)-ethyl]-1-phenxoy-2-hydroxy-3-amino-propane E — N-[2-(xanthyl-9)-ethyl]-1-(naphthoxy-1)-2-hydroxy-3-aminio-propane F — N-[2-(10,11-dihydro-5H-dibenzo-[a,d]-cycloheptene-5-yl)-ethyl]-1-(naphthoxy-1)-2-hydroxy-3-amino-propane G — N-[2-(10,11-dihydro-dibenzo-[b,e]-thiepine-11-yl)-ethyl]-1-(naphthoxy-1)-2-hydroxy-3-amino-propane H — N-[2-(thiaxanthyl-9)-ethyl]-1-phenoxy-2-hydroxy-3-aminopropane I — N-[2-(6,11-dihydro-dibenzo-[b,e]-oxepine-11-yl)-ethyl]-1-(3-methyl-phenoxy)-2-hydroxy-3-amino-propane J — N-[(6,11-dihydro-dibenzo-[b,e]-oxepine-11-yl)-ethyl]-1-(3-chlor-phenoxy)-2-hydroxy-3-amino-propane K — N-[2-(xanthyl-9)-ethyl]-1-(3-methyl-phenoxy)-2-hydroxy-3-aminio-propane L — N-[2-(xanthyl-99-ethyl]-1-(2-chlor-phenoxy)-2-hydroxy-3-amino-propane M — N-[2-(xanthyl-9)-1-(3-chlor-phenoxy)-2-hydroxy-3-amino-propane N — N-[(6,11-dihydro-dibenzo-[b,e]-oxepine-11-yl)-ethyl]-1-(naphthoxy-1)-2-hydroxy-3-amino-propane O — N-[2-(thiaxanthyl-9)-ethyl]-1-(2-chlor-phenoxy)-2-hydroxy-3-amino-propane P — N-[2-(thiaxanthyl-9)-ethyl]-1-(3-chlor-phenoxy)-2-hydroxy-3-amino-propane Q — N-[2-(thixanthyl-9)-ethyl]-1-(3-methyl-phenoxy)-2-hydroxy-3-amino-propane R — N-[2-(6,11-dihydro-dibenzo-[b,e]-oxepine-11-ylidene)-ethyl]-1-(naphthoxy-1)-2-hydroxy-3-amino-propane S — N-[2-(6,11-dihydro-dibenzo-[b,e]-oxepine-11-ylidene)-ethyl]-1-phenoxy-2-hydroxy-3-amino-propane T — N-[(6,11-dihydro-dibenzo-[b,e]-oxepine-11-yl)-ethyl]-1-cyclohexyloxy-2-hydroxy-3-amino-propane U — N-[2-(2-methyl-6,11-dihydro-dibenzo-[b,e]-oxepine-11-yl)-ethyl]-1-(3-methyl-phenoxy)-2-hydroxy-3-amino-propane V — N-[(6,11-dihydro-dibenzo-[b,e]-oxepine-11-yl)-ethyl]-1-(3-methyl-benzyloxy)-2-hydroxy-3-amino-propane W — N-[(6,11-dihyro-dibenzo-[b,e]-oxepine-11-yl)-ethyl]-1-(4-nitro-phenoxy)-2-hydroxy-3-amino-propane X — N-[2-(2-methoxy-6,11-dihydro-dibenzo-[b,e]-oxepine-11-yl)-ethyl]-1-(4-nitro-phenoxy)-2-hydroxy-3-amino-propane Y — N-[1-(6,11-dihydro-dibenzo-[b,e]-oxepine-11-yl)-butyl-2]-1-phenoxy-2-hydroxy-3-amino-propane Z — N-[2-(2-methoxy-6,11-dihydro-dibenzo-[b,e]-oxepine-11-yl)-ethyl]-1-phenoxy-2-hydroxy-3-ammino-propane AA — N-[(6,11-dihydro-dibenzo-[b,e]-oxepine-11-yl)-ethyl]-1-(2,3-dichlor-phenoxy)-2-hydroxy-3-amino-propane BB — N-[(6,11-dihydro-dibenzo-[b,e]-oxepine-11-yl)-ethyl]-1-(2,4-dichlor-phenoxy)-2-hydroxy-3-amino-propane
CC — N-[(6,11-dihydro-dibenzo-[b,e]-oxepine-11-yl)-ethyl]-1-(3,6-dichlor-phenoxy)-2-hydroxy-3-amino-propane
DD — N-[(6,11-dihydro-dibenzo-[b,e]-oxepine-11-yl)-ethyl]-1-(2,5-dichlor-phenoxy)-2-hydroxy-3-amino-propane
EE — N-[2-(2-chlor-6,11-dihydro-dibenzo-[b,e]-oxepine-11-yl)-ethyl]-1-phenoxy-2-hydroxy-3-amino-propane
FF — N-[2-(6,11-dihydro-dibenzo-[b,e]-oxepine-11-yl)-ethyl]-1-(4-chlor-phenoxy)-2-hydroxy-3-amino-propane
GG — N-[2-(6,11-dihydro-dibenzo-[b,e]-oxepine-11-yl)-ethyl]-1-(4-ethoxy-phenoxy)-2-hydroxy-3-amino-propane
HH — N-[2-(6,11-dihydro-dibenzo-[b,e]-oxepine-11-yl)-ethyl]-1-(cyclopentyloxy)-2-hydroxy-3-amino-propane
II — N-[2-(6,11-dihydro-dibenzo-[b,e]-oxepine-11-yl)-ethyl]-1-(cycloheptyloxy)-2-hydroxy-3-amino-propane
JJ — N-[2-(6,11-dihydro-dibenzo-[b,e]-oxepine-11-yl)-ethyl]-1-(cyclooctyloxy)-2-hydroxy-3-amino-propane
KK — N-[2-(6,11-dihydro-dibenzo-[b,e]-oxepine-11-yl)-ethyl]-1-(cyclohexylmethoxy)-2-hydroxy-3-amino-propane
LL — N-[2-(6,11-dihydro-dibenzo-[b,e]-oxepine-11-yl)-ethyl]-1-(3-methylcyclohexyloxy)-2-hydroxy-3-amino-propane
MM — N-[2-(6,11-dihydro-dibenzo-[b,e]-oxepine-11-yl)-ethyl]-1-(2-methylphenoxy)-2-hydroxy-3-amino-propane
NN — N-[2-(6,11-dihydro-dibenzo-[b,e]-oxepine-11-yl)-ethyl]-1-(4-methylphenoxy)-2-hydroxy-3-amino-propane
OO — N-[2-(6,11-dihydro-dibenzo-[b,e]-oxepine-11-yl)-ethyl]-1-[cyclododecyloxy]-2-hydroxy-3-amino-propane
PP — N-[2-(6,11-dihydro-dibenzo-[b,e]-oxepine-11-ylidene)-ethyl]-1-(3-methylphenoxy)-2-hydroxy-3-amino-propane
QQ — N-[2-(5H-dibenzo-[a,d]-cycloheptene-5-yl)-ethyl]-1-(naphthoxy-1)-2-hydroxy-3-amino-propane
RR — N-[2-(2-chlor-thiaxanthyl-9)-ethyl]-1-(3-methylphenoxy)-2-hydroxy-3-amino-propane
SS — N-[2-(6,11-dihydro-dibenzo-[b,e]-oxepine-11-yl)-ethyl]-1-(3-nitro-benzyloxy)-2-hydroxy-3-amino-propane
TT — N-[2-(6,11-dihydro-dibenzo-[b,e]-oxepine-11-yl)-ethyl]-1-(2-methylphenylmercapto)-2-hydroxy-3-amino-propane
UU — N-[2-(6,11-dihydro-dibenzo-[b,e]-oxepine-11-yl)-ethyl]-1-(3-methylphenylmercapto)-2-hydroxy-3-amino-propane
VV — N-methyl-N-[2-(6,11-dihydro-dibenzo-[b,e]-oxepine-11-yl)-ethyl]-1-(3-methylphenoxy)-2-hydroxy-3-amino-propane
WW — N-[2-(6,11-dihydro-dibenzo-[b,e]-oxepine-11-yl)-propyl-1]-1-(3-methylphenoxy)-2-hydroxy-3-amino-propane
XX — COMPLAMIN - xantinolnicotinate - 7- 2-hydroxy-3-(N-methyl-β-hydroxyethyl-amino)-propyl]-theopylline
YY — INPEA - 1-p-nitrophenyl-2-isopropyl-aminoethanol The compounds in accordance with the invention exhibit i.e., are possessed of special cardiac and circulatory activities and specificically of circulation stimulating and β-receptor blocking activities. As there are known structurally similar compounds possessed of these properties, in the test procedures the known compund COMPLAMIN-xantinolnicotinate-7-[2-hydroxy-3-(N-methyl-β-hydroxyethylamino)-propyl]-theophylline [circulatory stimulant] and 1-p-nitrophenyl-2-isopropylaminoethanol (INPEA, see Med. Pharmacol. exp. 15, 1966 p. 73; Boll. Chim. Farm. 105, 1966) [β-receptor blocker] were employed as comparison compounds.

TABLE

INCREASE IN THE BLOOD TIME VOLUME IN THE AORTA OF UNANESTHETIZED DOGS (1) AND INHIBITION OF GLYCOGEN CATABOLISM FOLLOWING HYPOXIA IN UNANESTHETIZED RATS (2)

| COMPOUND | 1. INCR. IN BLOOD CIRCULATION (UNANESTHETIZED DOGS) | | 2. β-RECEPTOR BLOCKING (RATS) | |
|---|---|---|---|---|
| | DOSES MG/KG ORAL | MAX. INCREASE OF BLOOD TIME VOLUME IN % AS COMPARED TO THE CONTROL (=100%) | DOSES MG/KG I.P. | GLYCOGEN CONTENT OF THE MYOCARDIUM AFTER HYPOXIA (mg %) |
| XX | 25.0 | 110 | — | — |
| CONTROL | — | — | — | 15 |
| YY | — | — | 20 | 38 |
| A | — | — | 20 | 165 |
| B | 0.5 | 115 | 20 | 172 |
| C | 0.5 | 123 | 1 | 193 |
| D | 0.1 | 200 | 20 | 45 |
| E | 0.5 | 140 | 20 | 170 |
| F | 0.5 | 115 | 20 | 195 |
| G | 0.5 | 148 | 20 | 169 |
| H | 0.5 | 153 | 20 | 48 |
| I | 0.5 | 115 | 1 | 135 |
| U | 0.5 | 177 | 20 | 310 |
| K | 0.5 | 110 | 10 | 232 |
| L | 0.5 | 124 | — | — |
| M | 0.5 | 110 | — | — |
| N | 0.5 | 215 | 10 | 70 |
| O | 0.5 | 180 | — | — |
| P | 0.5 | 150 | 10 | 158 |
| Q | 0.5 | 168 | — | — |
| R | 0.5 | 115 | 10 | 297 |

TABLE-continued

INCREASE IN THE BLOOD TIME VOLUME IN THE AORTA OF UNANESTHE-
TIZED DOGS (1) AND INHIBITION OF GLYCOGEN CATABOLISM
FOLLOWING HYPOXIA IN UNANESTHETIZED RATS (2)

| | 1. INCR. IN BLOOD CIRCULATION (UNANESTHETIZED DOGS) | | 2. β-RECEPTOR BLOCKING (RATS) | |
|---|---|---|---|---|
| COMPOUND | DOSES MG/KG ORAL | MAX. INCREASE OF BLOOD TIME VOLUME IN % AS COMPARED TO THE CONTROL (=100%) | DOSES MG/KG I.P. | GLYCOGEN CONTENT OF THE MYOCARDIUM AFTER HYPOXIA (mg %) |
| S | 0.25 | 220 | — | — |
| T | 1.0 | 160 | 3 | 7 |
| U | 0.25 | 120 | 3 | 15 |
| V | 0.5 | 125 | 10 | 93 |
| W | 0.25 | 120 | 3 | 79 |
| X | 0.5 | 120 | 3 | 34 |
| Y | 0.5 | 180 | 10 | 52 |
| Z | 0.5 | 190 | — | — |
| AA | 0.5 | 115 | 1 | 29 |
| BB | 0.5 | 120 | 1 | 18 |
| CC | 0.5 | 129 | 1 | 33 |
| DD | 0.5 | 115 | 1 | 12 |
| EE | 0.5 | 140 | — | — |
| FF | 0.5 | 135 | 1 | 21 |
| GG | 0.5 | 275 | 1 | 21 |
| HH | 0.5 | 150 | — | — |
| II | 0.5 | 180 | — | — |
| JJ | 0.5 | 125 | — | — |
| KK | 0.5 | 115 | — | — |
| LL | 0.5 | 115 | 3 | 40 |
| MM | 0.5 | 150 | 3 | 89 |
| NN | 0.5 | 115 | 1 | 21 |
| OO | — | — | 1 | 32 |
| PP | — | — | 10 | 212 |
| QQ | — | — | 3 | 84 |
| RR | — | — | 3 | 79 |
| SS | — | — | 1 | 41 |
| TT | — | — | 1 | 49 |
| UU | — | — | 1 | 25 |
| VV | — | — | 3 | 28 |
| WW | — | — | 3 | 79 |

Results

1. It can be seen from the preceding Table that 25.0 mg/kg xantinolnicotinate (oral) produced an increase in the heart minute volume of from 100 to 110%. The result was reproducible in each instance so that it can be taken as the comparison value. The novel compounds of the invention were administered in a dosage range of from 0.25 to 1.0 mg/kg per os i.e., in doses lower by 2 powers of 10. This consequently establishes for the compounds of the invention a marked superiority with respect to effect produced i.e., increase in heart minute volume and this was true for every compound tested.

2. With respect to the β-receptor blocking activity as measured by glycogen content of the myocardium after induced hypoxia, it must be taken into consideration that the normal glycogen content of normal untreated rats amounts on the average to 225 mg%. In untreated rats, subjected to hypoxia it decreases to 15 mg%. The comparison compound INPEA administered in an amount of 20 mg/kg intraperitoneally had an inhibiting effect whereby the glycogen content was decreased to only 38 mg%. All of the novel compounds in accordance with the invention which resulted in an inhibition of the glyocen content which was less than that of the INPEA i.e., the final content of glycogen in the myocardium is greater than 38% with equal or lower dosages, are more effective than INPEA. Those compounds which when employed in lower dosges than the comparison compound and which still produce an inhibiting effect are also superior as it can be expected that with an increased dosage, a more marked inhibition will be observed, than shown by the comparison compound.

This it can be seen that the compounds of the invention administered in low dosages (0.1 - 0.5 mg/kg, oral) produce in the unanesthetized dog an increase in the peripheral blood circulation of the organs by an emptying of the venous blood storage depots i.e., through an increase of the heart minute volume. Administered in higher doses (1–20 mg/kg, intraperitoneally) the compounds of the invention effect a blocking of the cardiac β-receptors in rats.

As indicated hereinbefore, the compounds of the present invention are useful for the treatment of conditions associated with cardiac and impaired circulatory phenomena and for this purpose the active compounds are associated with a pharmaceutically acceptable carrier in a form suitable for administration both perorally or parenterally.

For example, for oral administration the active compounds can be administered in liquid or solid dosage forms. Solid forms include capsules, tablets, powders, pills and the like and the liquid forms include suitably flavored aqueous suspensions and solutions (depending on concentration desired) and flavored oil suspensions and solutions wherein edible oils such as corn oil, cotton seed oil, coconut oil, peanut oil, sesame oil or mixtures of these and the like can be employed.

For preparing compounds such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administration.

The dosage of the novel compounds of the present invention for the treatment of the conditions as set out above, depends on the age, weight and condition of he patient being treated. Generally speaking, for adult oral administration, the preferred unit dosage is 1 mg –50 mg of active compound with a sutiable pharmaceutical diluent and/or lubricant.

We claim:

1. A tricyclic aminoalkyl derivative selected from the group consisting of
 a. compounds of the formula:

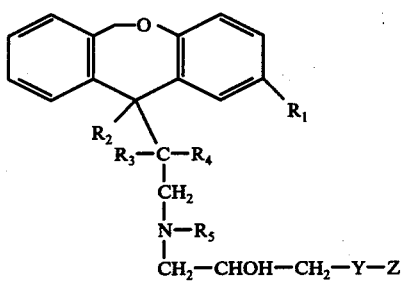

wherein
 $R_1$ is a member selected from the group consisting of hydrogen, chloro, lower alkyl and lower alkoxy;
 $R_2$ is hydrogen or hydroxyl;
 $R_3$ is hydrogen;
 $R_4$ and $R_5$ are each hydrogen or lower alkyl;
 Y is oxygen or sulfur; and
 Z is cycloalkyl, lower alkylcycloalkyl and cycloalkyl-lower alkyl containing from 5 to 12 ring-carbon atoms, unsubstituted or mono- or disubstituted benzyl and aryl of up to 10 carbon atoms, wherein said substituents are chloro, nitro, lower alkoxy, benzyloxy, lower alkyl or trifluoromethyl; and
 b. pharmaceutically acceptable acid addition salts thereof.

2. A compound according to claim 1 wherein said compound is designated N-[2-(6,11-dihydro-dibenzo-[b,e]-oxepine-11-yl)-ethyl]-1-phenoxy-2-hydroxy-3-amino-propane.

3. A compound according to claim 1 wherein said compound is designated N-[2-(6,11-dihydro-dbenzo-[b,e]-oxepine-11-yl)-ethyl]-1-(3-methyl-phenoxy)-2-hydroxy-3-amino-propane.

4. A compound according to claim 1 wherein said compound is designated N-[(6,11-dihydro-dibenzo-[b,e]-oxepine-11-yl) ethyl]-1-(naphthoxy-1)-2-hydroxy-3-amino-propane.

5. A compound according to claim 1 wherein said compound is designated N-[2-(6,11-dihydro-dibenzo-[b,e]-oxepine-11-yl)-ethyl]-1-(4-ethoxy-phenoxy)-2-hydroxy-3-amino-propane.

6. Tricyclic aminoalkyl compound as claimed in claim 1 wherein $R_1$ is hydrogen.

7. Tricyclic aminoalkyl compound as claimed in claim 1 wherein $R_1$ is chloro.

8. Tricyclic aminoalkyl compound as claimed in claim 1 wherein $R_1$ is lower alkyl or lower alkoxy.

9. Tricyclic aminoalkyl compound as claimed in claim 1 wherein $R_2$ is hydrogen.

10. Tricyclic aminoalkyl compound as claimed in claim 1 wherein $R_2$ is hydroxyl.

11. Tricyclic aminoalkyl compound as claimed in claim 1 wherein one of $R_4$ and $R_5$ is hydrogen.

12. Tricyclic aminoalkyl compound as claimed in claim 1 wherein one of $R_4$ and $R_5$ is alkyl.

13. Tricyclic aminoalkyl compound as claimed in claim 1 wherein Y is oxygen.

14. Tricyclic aminoalkyl compound as claimed in claim 1 wherein Y is sulfur.

15. Tricyclic aminoalkyl compound as claimed in claim 1 wherein Z is cycloalkyl or lower alkylcycloalkyl.

16. Tricyclic aminoalkyl compound as claimed in claim 1 wherein Z is cycloalkyl-lower alkyl.

17. Tricyclic aminoalkyl compound as claimed in claim 1 wherein Z is unsubstituted benzyl or aryl.

18. Tricyclic aminoalkyl compound as claimed in claim 1 wherein Z is substituted benzyl.

19. Tricyclic aminoalkyl compound as claimed in claim 1 wherein Z is substituted aryl.

* * * * *